United States Patent [19]

Conrad et al.

[11] Patent Number: 4,540,779
[45] Date of Patent: Sep. 10, 1985

[54] CRYSTALLINE 7-(R)-AMINO-3-(1'PYRIDINIUMMETHYL)-CEPH-3-EM-4-CARBOXYLATE MONOHYDROCHLORIDE MONOHYDRATE COMPOUND

[75] Inventors: Preston C. Conrad, Indianapolis; Alvydas A. Jarmas, Speedway, both of Ind.

[73] Assignee: Eli Lilly and Company, Indianapolis, Ind.

[21] Appl. No.: 505,662

[22] Filed: Jun. 20, 1983

[51] Int. Cl.$^3$ .................... C07D 501/38; A61K 31/44
[52] U.S. Cl. .......................................... 544/24; 544/25
[58] Field of Search .................... 544/25, 24; 424/246

[56] References Cited

U.S. PATENT DOCUMENTS 3,207,755  9/1965  Abraham et al. .................... 260/243
4,258,041  3/1981  O'Callaghan et al. .............. 424/246
4,369,313  1/1983  Jones et al. ............................ 544/24

FOREIGN PATENT DOCUMENTS 2052490A  1/1981  United Kingdom .

Primary Examiner—Nicholas S. Rizzo
Attorney, Agent, or Firm—Paul C. Steinhardt; Arthur R. Whale

[57] ABSTRACT

Crystalline 7-(R)-amino-3-(1'-pyridiniummethyl)-ceph-3-em-4-carboxylate monohydrochloride monohydrate compound is an intermediate in the synthesis of the cephalosporin antibiotic ceftazidime.

1 Claim, No Drawings

CRYSTALLINE 7-(R)-AMINO-3-(1'PYRIDINIUMMETHYL)-CEPH-3-EM-4-CARBOXYLATE MONOHYDROCHLORIDE MONOHYDRATE COMPOUND

SUMMARY

This invention relates to an intermediate in the synthesis of the cephalosporin antibiotic 7-(R)-[2-(2'-amino-1',3'-thiazol-4'-yl)-2-(Z)-((2',2'-dimethyl-2'-yl acetic acid)oximino ether)-acetamido]-3-(1'-pyridiniummethyl)-ceph-3-em-4-carboxylate, also known as ceftazidime, which is represented in Formula 1

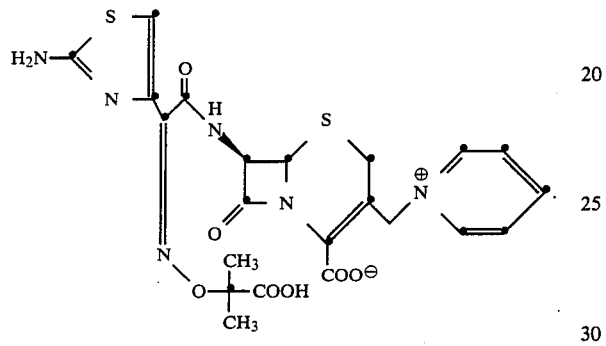

Ceftazidime is described in U.S. Pat. No. 4,258,041, issued Mar. 24, 1981. The antibiotic possesses excellent activity against a broad spectrum of both gram-positive and gram-negative pathogens.

In the production of such an important antibiotic as ceftazidime, it is advantageous to have synthetic intermediates that are readily made in a highly pure crystalline salt form which, in addition, are stable under inexpensive storage conditions for long periods of time.

The instant invention provides such a crystalline, highly stable synthetic intermediate for the production of ceftazidime, namely the crystalline monohydrochloride monohydrate form of zwitterionic 7-(R)-amino-3-(1'-pyridiniummethyl)-ceph-3-em-4-carboxylate.

DETAILED DESCRIPTION

This invention encompasses the crystalline monohydrochloride monohydrate form of the zwitterionic compound 7-(R)-amino-3-(1'-pyridiniummethyl)-ceph-3-em-4-carboxylate, which compound is represented by the following Formula 2:

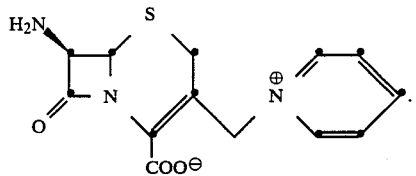

The crystalline monohydrochloride monohydrate form of the compound of Formula 2 (hereinafter referred to as the "monohydrochloride monohydrate compound") is a white microcrystalline solid which is characterized by its X-ray powder diffraction pattern listed in Table 1 below. The diffraction pattern was obtained with nickel-filtered copper radiation (Cu:Ni) of wave length $\lambda = 1.5418$ Å. The interplanar spacings are in the column headed by "d" and the relative intensities in the column "$I/I_1$". (The abbreviation "b" stands for "broad").

TABLE 1

| d | $I/I_1$ |
|---|---|
| 10.75 | .47 |
| 8.17 | 1.00 |
| 6.31 | .20 |
| 5.74 | .33 |
| 5.35 | .20 b |
| 4.95 | .13 |
| 4.84 | .07 |
| 4.47 | .93 |
| 4.25 | .53 |
| 4.08 | 1.00 |
| 3.81 | .20 |
| 3.67 | .07 |
| 3.52 | .33 |
| 3.44 | .13 |
| 3.29 | .07 |
| 3.14 | .53 |
| 3.01 | .27 |
| 2.90 | .10 |
| 2.80 | .47 |
| 2.74 | .27 |
| 2.63 | .07 |
| 2.53 | .20 |
| 2.47 | .07 |
| 2.41 | .03 |
| 2.38 | .27 |
| 2.27 | .27 |
| 2.20 | .10 |
| 2.11 | .03 b |
| 2.06 | .03 b |
| 1.992 | .17 |
| 1.948 | .07 |
| 1.893 | .10 b |
| 1.837 | .13 |

The monohydrochloride monohydrate compound is made by dissolving the dihydrochloride dihydrate form of the compound represented by Formula 2 (hereinafter referred to as the "dihydrochloride dihydrate compound") in an aqueous solvent system and inducing crystallization by the addition of dimethylacetamide. Acceptable solvent systems include methanol/water, ethanol/water and acetone/water systems, with a 1:1 v:v methanol/water solvent system being preferred. The precipitation procedure can be carried out at a temperature between about 25° C. to about 40° C. The resultant crystals of monohydrochloride monohydrate compound are isolated by filtration and are dried in vacuo at a temperature between about 25° C. to about 40° C.

The starting material in the synthesis of the instant monohydrochloride monohydrate compound, i.e. the corresponding dihydrate dihydrochloride, is made by cleaving the side chain (N-deacylation) of 7-(R)-(2-(thien-2-yl)acetamido)-3-(1-pyridiniummethyl)ceph-3-em-4-carboxylate, also known as "cephaloridine". The side chain of cephaloridine is cleaved by first silylating the compound, treating the silylated derivative with phosphorous pentachloride, and finally by adding isopropanol or butanediol. The precipitate of 7-(R)-amino deacylated product thus obtained is dissolved in hydrochloric acid and precipitated by the addition of isopropanol to give the dihydrochloride dihydrate compound.

An experimental procedure of the above synthesis of the dihydrochloride dihydrate compound is given in Preparation 10 (column 17) of O'Callaghan et al., U.S. Pat. No. 4,258,041, issued Mar. 24, 1981, which entire patent is herein incorporated by reference.

The monohydrochloride monohydrate compound of the instant invention is an intermediate in the synthesis of the broad spectrum antibiotic ceftazidime, represented by Formula 1 above. More specifically, the compound represented by the following Formula 3

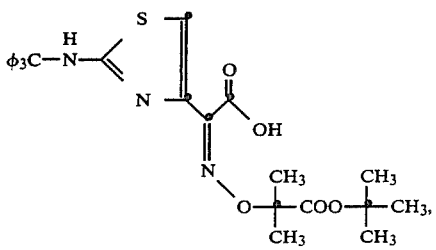

(2-(2'-tritylamino)-1',3'-thiazol-4'-yl)-2-(Z)-((t-butyl 2',2'-dimethyl-2'-yl acetate)oximino ether) acetic acid) is converted to the corresponding acid chloride with phosphorus pentachloride. The instant monohydrochloride monohydrate compound is acylated with the acid chloride to give 7-(R)-[2'-(2''-(tritylamino)-1'',3''-thiazol-4''-yl)-2'-(Z)-((t-butyl 2'',2''-dimethyl-2''-yl acetate) oxime ether)acetamido]-3-(1'-pyridiniummethyl)-ceph-3-em-4-carboxylate, referred to hereinafter as "blocked ceftazidime". The amino and carboxy protecting groups are removed from the blocked ceftazidime compound by sequential treatment with concentrated formic acid and concentrated hydrochloric acid to give ceftazidime (Formula 1 above) as the dihydrochloride form.

The conversion of the compound of the Formula 3 to blocked ceftazidime is discussed further below in the Experimental Section. The conversion of blocked ceftazidime to the dihydrochloride form of ceftazidime is discussed in O'Callaghan et al., U.S. Pat. No. 4,258,041, especially in columns 23 and 24.

EXPERIMENTAL

In the following experimental section, the infrared spectra were taken on a Nicolet MX-1 instrument. The ultraviolet spectra were obtained on a Varian Associates Cary 118 instrument. The nuclear magnetic resonance spectra were taken at 90 MHz on a Varian Associates EM-390 instrument. The mass spectra were obtained on a Varian Associates MAT 731 instrument.

In the following discussion, the abbreviations "mmol", "v:v", "i.r.", "m.s.", "u.v.", and "n.m.r." stand for millimole, volume to volume, infrared spectrum, mass spectrum, ultraviolet spectrum, and nuclear magnetic resonance spectrum, respectively. With respect to the nuclear magnetic resonance spectra, the abbreviations "d", "br s", "q", and "DMSO-d$_6$" stand for doublet, broad singlet, quartet, and dimethylsulfoxide in which all the protons have been replaced with deuterium, respectively.

The following preparations and examples are meant to further explain the instant invention and not to limit the invention's scope.

PREPARATION 1

7-(R)-[2'-(2''-(Tritylamino)-1'',3''-thiazol-4''-yl)-2'-(Z)-((t-butyl-2'',2''-dimethyl-2''-yl-acetate)oxime ether)acetamido]-3-(1'-pyridiniummethyl)-ceph-3-em-4-carboxylate Phosphorus pentachloride (0.6 g, 2.98 mmol) was added to dry methylene chloride (10 ml) and the resultant solution was cooled to 0° C. 2-(2'-Tritylamino)-1',3'-thiazol-4'-yl)-2-(Z)-((t-butyl-2',2'-dimethyl-2'-yl-acetate)oxime ether)acetic acid (1.55 g, 2.71 mmol) was added to the solution and the solution was stirred for 30 minutes at 0° C. To this solution was added a cold solution of water (7.5 ml) and triethylamine (0.9 ml), and the resultant heterogeneous mixture was stirred for 3 minutes at 0° C. The aqueous phase was separated and discarded. The remaining cold (0° C.) methylene chloride phase was then added to a cooled (0° C.) slurry of 7-(R)-amino-3-(1'-pyridiniummethyl)-ceph-3-em-4-carboxylate monohydrochloride monohydrate (0.78 g. 2.25 mmol), dimethylacetamide (8 ml) and triethylamine (1.73 ml, 12.43 mmol) over a seven-minute period. The reaction mixture was stirred at 0° C. for 60 minutes. The reaction was quenched by the addition of cold (0° C.) water (18 ml), which dissolved the precipitate. The aqueous phase is separated from the organic phase and then extracted with methylene chloride (5 ml, 1X). To the combined methylene chloride extracts was added dimethylacetamide (8 ml) and diethyl ether (18 ml). The solution was heated and crystallization was allowed to take place over a thirty-minute period. The resultant thick slurry was cooled to 0° C. for two hours, and the precipitate was collected by filtration, then washed with a 5% dimethylacetamide/diethyl ether solution (20 ml, 1X). The precipitate was dried for 16 hours in vacuo at 40° C. to give 1.56 g (1.85 mmol) of 7-(R)-[2'-(2''-(tritylamino)-1'',3''-thiazol-4''-yl)-2''-(Z)-((t-butyl-2'',2''-dimethyl-2''-yl-acetate)oxime ether)-acetamido]-3-(1'-pyridiniummethyl)-ceph-3-em-4-carboxylate.

EXAMPLE 1

7-(R)-Amino-3-(1'-pyridiniummethyl)ceph-3-em-4-carboxylate monohydrochloride monohydrate 7-(R)-Amino-3-(1'-pyridiniummethyl)-ceph-3-em-4-carboxylate dihydrochloride dihydrate (12.5 g, 31.25 mmol) was dissolved in 50% methanol/water at ambient temperature. Dimethylacetamide (50 ml) was slowly added to the resultant solution. Crystallization of the monohydrochloride monohydrate began soon after the addition of dimethylacetamide was begun. Upon completion of the addition of the dimethylacetamide, the reaction mixture was cooled to 5° C. for approximately 1 hour. The reaction mixture was filtered and the resultant precipitate was washed with cold (0° C.) dimethylacetamide (25 ml, 1X). The precipitate was then dried in vacuo at 40° C. for 16 hours yielding 7.94 g, 73.6% (23 mmol) of 7-(R)-amino-3-(1'-pyridiniummethyl)ceph-3-em-4-carboxylate: n.m.r. (DMSO-d$_6$) δ9.3 (d, J=6 Hz, pyridinium protons), 8.7 (dd, 1, J=6, 6 Hz, pyridinium protons), 8.2 (dd, 2, J=6, 6 Hz, pyridinium protons), 5.7 (br. s, 2, C-6 and C-7 protons), 5.1 (ABq, J=5 Hz, 3'-methylene protons), 3.5 (ABq, 2, J=18 Hz, C-2 methylene protons).

We claim:
1. The crystalline monohydrochloride monohydrate of 7-(R)-amino-3-(1'-pyridiniummethyl)-ceph-3-em-4-carboxylate which has the following X-ray powder diffraction obtained with nickel-filtered copper radiation of λ=1.5418 Å wherein d represents the interplanar spacing and I/I$_1$ the relative intensity:

| d | I/I$_1$ |
|---|---|
| 10.75 | .47 |
| 8.17 | 1.00 |

-continued

| d | I/I$_1$ |
|---|---|
| 6.31 | .20 |
| 5.74 | .33 |
| 5.35 | .20 b |
| 4.95 | .13 |
| 4.84 | .07 |
| 4.47 | .93 |
| 4.25 | .53 |
| 4.08 | 1.00 |
| 3.81 | .20 |
| 3.67 | .07 |
| 3.52 | .33 |
| 3.44 | .13 |
| 3.29 | .07 |
| 3.14 | .53 |
| 3.01 | .27 |

-continued

| d | I/I$_1$ |
|---|---|
| 2.90 | .10 |
| 2.80 | .47 |
| 2.74 | .27 |
| 2.63 | .07 |
| 2.53 | .20 |
| 2.47 | .07 |
| 2.41 | .03 |
| 2.38 | .27 |
| 2.27 | .27 |
| 2.20 | .10 |
| 2.11 | .03 b |
| 2.06 | .03 b |
| 1.992 | .17 |
| 1.948 | .07 |
| 1.893 | .10 b |
| 1.837 | .13. |

* * * * *